(12) United States Patent
Edelman et al.

(10) Patent No.: US 8,444,669 B2
(45) Date of Patent: May 21, 2013

(54) EMBOLIC FILTER DELIVERY SYSTEM AND METHOD

(75) Inventors: Peter Edelman, Maple Grove, MN (US); Lawrence Wasicek, San Jose, CA (US); Nayan Ashar, San Jose, CA (US); Husnija Mujkanovic, Santa Clara, CA (US); Eddie Sucgang, South San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 649 days.

(21) Appl. No.: 12/563,758

(22) Filed: Sep. 21, 2009

(65) Prior Publication Data

US 2010/0152829 A1    Jun. 17, 2010

Related U.S. Application Data

(60) Provisional application No. 61/122,575, filed on Dec. 15, 2008.

(51) Int. Cl.
*A61F 2/01* (2006.01)

(52) U.S. Cl.
USPC .......................... 606/200; 623/1.11; 623/1.12

(58) Field of Classification Search
None
See application file for complete search history.

(56) References Cited

U.S. PATENT DOCUMENTS

| 3,472,230 A | 10/1969 | Fogarty |
| 3,592,186 A | 7/1971 | Oster |
| 3,683,904 A | 8/1972 | Forster |
| 3,889,657 A | 6/1975 | Baumgarten et al. |
| 3,952,747 A | 4/1976 | Kimmell |
| 3,996,938 A | 12/1976 | Clark |
| 4,046,150 A | 9/1977 | Schwartz |
| 4,279,593 A | 7/1981 | Rohlcke |

(Continued)

FOREIGN PATENT DOCUMENTS

| DE | 2821048 B1 | 11/1979 |
| DE | 3107392 A1 | 9/1982 |

(Continued)

OTHER PUBLICATIONS

"Atherosclerotic Disease of the Aortic Arch as a Risk Factor of Recurrent Ischemic Stroke,"The New England Journal of Medicine , pp. 1216-1221 (May 1996).

(Continued)

*Primary Examiner* — Thomas J Sweet
*Assistant Examiner* — Christopher D Prone
(74) *Attorney, Agent, or Firm* — Seager, Tufte & Wickhem LLC

(57) ABSTRACT

The disclosure pertains to a medical device deployment system comprising a restraint member which holds the embolic protection filter in a restrained, or partially collapsed, state for insertion into a lumen and transit to a desired deployment site. The restraint member comprises two or more portions which differ in their mechanical ability to resist the radial forces exerted by various portions of the medical device when it is in a restrained, or partially collapsed, state. The restraint member is maintained in a restraint configuration by an actuation member which engages portions of the restraint member lying on opposite sides of a generally axial gap until deployment of the medical device is desired. Withdrawal of the actuation member allows the restraint member to release the medical device which may then return to a deployed state. The invention also provides a method for assembling a medical device deployment system.

14 Claims, 9 Drawing Sheets

U.S. PATENT DOCUMENTS

| | | | |
|---|---|---|---|
| 4,413,989 A | 11/1983 | Schjeldahl et al. |
| 4,425,908 A | 1/1984 | Simon |
| 4,447,227 A | 5/1984 | Kotsanis |
| 4,580,568 A | 4/1986 | Gianturco |
| 4,590,938 A | 5/1986 | Segura et al. |
| 4,619,246 A | 10/1986 | Molgaard-Nielsen |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa |
| 4,669,469 A | 6/1987 | Gifford, III et al. |
| 4,705,517 A | 11/1987 | DiPisa |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz et al. |
| 4,790,812 A | 12/1988 | Hawkins |
| 4,790,813 A | 12/1988 | Kensey |
| 4,793,348 A | 12/1988 | Palmaz |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGuirr |
| 4,842,579 A | 6/1989 | Shiber |
| 4,857,045 A | 8/1989 | Rydell |
| 4,857,046 A | 8/1989 | Stevens |
| 4,867,157 A | 9/1989 | McGurk-Burleson et al. |
| 4,873,978 A | 10/1989 | Ginsburg |
| 4,886,061 A | 12/1989 | Fischell |
| 4,898,575 A | 2/1990 | Fischell |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Gifford et al. |
| 4,946,466 A | 8/1990 | Pinchuk |
| 4,950,277 A | 8/1990 | Farr |
| 4,955,895 A | 9/1990 | Sugiyama |
| 4,957,482 A | 9/1990 | Shiber |
| 4,964,409 A | 10/1990 | Tremulis |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,026,377 A | 6/1991 | Burton |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin |
| 5,071,425 A | 12/1991 | Gifford |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang |
| 5,100,425 A | 3/1992 | Fischell |
| 5,102,415 A | 4/1992 | Guenther |
| 5,104,399 A | 4/1992 | Lazarus |
| 5,108,419 A | 4/1992 | Reger et al. |
| 5,133,733 A | 7/1992 | Rasmussen |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,224,953 A | 7/1993 | Morgentaler |
| 5,226,909 A | 7/1993 | Evans |
| 5,306,286 A | 4/1994 | Stack |
| 5,314,444 A | 5/1994 | Gianturco |
| 5,314,472 A | 5/1994 | Fontaine |
| 5,315,996 A | 5/1994 | Lundquist |
| 5,318,576 A | 6/1994 | Plassche |
| 5,329,942 A | 7/1994 | Gunther |
| 5,330,484 A | 7/1994 | Gunther |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazarus |
| 5,399,165 A | 3/1995 | Paul |
| 5,405,377 A | 4/1995 | Cragg |
| 5,405,378 A | 4/1995 | Strecker |
| 5,409,454 A | 4/1995 | Fischell et al. |
| 5,415,630 A | 5/1995 | Gory |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun |
| 5,437,288 A | 8/1995 | Schwartz et al. |
| 5,441,483 A | 8/1995 | Avitall |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson |
| 5,476,104 A | 12/1995 | Sheahon |
| 5,484,418 A | 1/1996 | Quiachon et al. |
| 5,490,859 A | 2/1996 | Mische et al. |
| 5,497,785 A | 3/1996 | Viera |
| 5,507,767 A | 4/1996 | Maeda et al. |
| 5,509,899 A | 4/1996 | Fan et al. |
| 5,512,044 A | 4/1996 | Duer |
| 5,527,354 A | 6/1996 | Fontaine |
| 5,536,242 A | 7/1996 | Willard et al. |
| 5,540,707 A | 7/1996 | Ressemann et al. |
| 5,549,626 A | 8/1996 | Miller |
| 5,562,724 A | 10/1996 | Vorwerk et al. |
| 5,569,274 A | 10/1996 | Rapacki et al. |
| 5,569,275 A | 10/1996 | Kotula et al. |
| 5,599,492 A | 2/1997 | Engelson |
| 5,601,568 A | 2/1997 | Chevillon |
| 5,605,543 A | 2/1997 | Swanson |
| 5,634,897 A | 6/1997 | Dance |
| 5,634,942 A | 6/1997 | Chevillon et al. |
| 5,643,278 A * | 7/1997 | Wijay .................... 623/1.11 |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers |
| 5,707,359 A | 1/1998 | Bufalini |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren |
| 5,749,848 A | 5/1998 | Jang et al. |
| 5,769,816 A | 6/1998 | Barbut et al. |
| 5,779,716 A | 7/1998 | Cano |
| 5,782,809 A | 7/1998 | Umeno |
| 5,792,157 A | 8/1998 | Mische et al. |
| 5,792,300 A | 8/1998 | Inderbitzen |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,807,330 A | 9/1998 | Teitelbaum |
| 5,807,398 A | 9/1998 | Shaknovich |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,632 A | 11/1998 | Jacobsen et al. |
| 5,833,644 A | 11/1998 | Zadno-Azizi et al. |

| | | |
|---|---|---|
| 5,833,650 A | 11/1998 | Imran |
| 5,836,969 A | 11/1998 | Kim et al. |
| 5,843,050 A | 12/1998 | Jones et al. |
| 5,846,260 A | 12/1998 | Maahs |
| 5,846,261 A | 12/1998 | Kotula et al. |
| 5,848,964 A | 12/1998 | Samuels |
| 5,873,906 A | 2/1999 | Lau et al. |
| 5,876,367 A | 3/1999 | Kaganov et al. |
| 5,893,867 A | 4/1999 | Bagaoisan et al. |
| 5,895,399 A | 4/1999 | Barbut et al. |
| 5,895,407 A | 4/1999 | Jayaraman |
| 5,902,263 A | 5/1999 | Patterson et al. |
| 5,906,618 A | 5/1999 | Larson |
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |
| 5,919,225 A | 7/1999 | Lau et al. |
| 5,921,924 A | 7/1999 | Avitall |
| 5,925,016 A | 7/1999 | Chornenky |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,941,869 A | 8/1999 | Patterson et al. |
| 5,941,896 A | 8/1999 | Kerr |
| 5,947,995 A | 9/1999 | Samuels |
| 5,951,585 A | 9/1999 | Cathcart et al. |
| 5,954,745 A | 9/1999 | Gertler |
| 5,976,172 A | 11/1999 | Homsma |
| 5,980,555 A | 11/1999 | Barbut et al. |
| 5,989,210 A | 11/1999 | Morris et al. |
| 5,989,271 A | 11/1999 | Bonnette et al. |
| 5,989,281 A | 11/1999 | Barbut et al. |
| 5,993,469 A | 11/1999 | McKenzie |
| 5,997,557 A | 12/1999 | Barbut et al. |
| 6,001,118 A | 12/1999 | Daniel et al. |
| 6,004,279 A | 12/1999 | Crowley et al. |
| 6,007,557 A | 12/1999 | Ambrisco et al. |
| 6,007,558 A | 12/1999 | Ravenscroft |
| 6,010,522 A | 1/2000 | Barbut et al. |
| 6,013,085 A | 1/2000 | Howard |
| 6,019,787 A | 2/2000 | Richard et al. |
| 6,022,336 A | 2/2000 | Zadno-Azizi et al. |
| 6,027,520 A | 2/2000 | Tsugita et al. |
| 6,039,744 A | 3/2000 | Forber |
| 6,042,598 A | 3/2000 | Tsugita et al. |
| 6,048,338 A | 4/2000 | Larson |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson |
| 6,066,158 A | 5/2000 | Engelson |
| 6,068,645 A | 5/2000 | Tu |
| 6,086,605 A | 7/2000 | Barbut et al. |
| 6,099,549 A | 8/2000 | Bosma et al. |
| 6,117,154 A | 9/2000 | Barbut et al. |
| 6,126,685 A | 10/2000 | Lenker et al. |
| 6,129,739 A | 10/2000 | Khosravi |
| 6,136,016 A | 10/2000 | Barbut et al. |
| 6,142,987 A | 11/2000 | Tsugita |
| 6,146,396 A | 11/2000 | Konya |
| 6,152,946 A | 11/2000 | Broome et al. |
| 6,165,200 A | 12/2000 | Tsugita et al. |
| 6,168,579 B1 | 1/2001 | Tsugita |
| 6,168,603 B1 | 1/2001 | Leslie et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates |
| 6,179,851 B1 | 1/2001 | Barbut et al. |
| 6,179,859 B1 | 1/2001 | Bates |
| 6,179,860 B1 | 1/2001 | Fulton, III et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,217,567 B1 | 4/2001 | Zadno-Azizi et al. |
| 6,221,006 B1 | 4/2001 | Dubrul |
| 6,224,620 B1 | 5/2001 | Maahs |
| 6,231,544 B1 | 5/2001 | Tsugita |
| 6,235,044 B1 | 5/2001 | Root et al. |
| 6,235,045 B1 | 5/2001 | Barbut |
| 6,238,412 B1 | 5/2001 | Dubrul |
| 6,245,087 B1 | 6/2001 | Addis |
| 6,245,088 B1 | 6/2001 | Lowery |
| 6,245,089 B1 | 6/2001 | Daniel et al. |
| 6,254,628 B1 | 7/2001 | Wallace et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,352,561 B1 | 3/2002 | Leopold et al. |
| 6,355,051 B1 | 3/2002 | Sisskind |
| 6,361,545 B1 | 3/2002 | Macoviak et al. |
| 6,383,206 B1 | 5/2002 | Gillick et al. |
| 6,394,017 B2 | 5/2002 | Pavon |
| 6,423,086 B1 | 7/2002 | Barbut |
| 6,447,540 B1 | 9/2002 | Fontaine et al. |
| 6,468,298 B1 | 10/2002 | Pelton |
| 6,485,501 B1 | 11/2002 | Green |
| 6,537,295 B2 | 3/2003 | Petersen |
| 6,558,396 B1 | 5/2003 | Inoue |
| 6,562,058 B2 | 5/2003 | Seguin et al. |
| 6,673,053 B2 | 1/2004 | Wang et al. |
| 6,878,153 B2 | 4/2005 | Linder et al. |
| 6,951,570 B2 | 10/2005 | Linder et al. |
| 6,962,598 B2 | 11/2005 | Linder et al. |
| 6,997,939 B2 | 2/2006 | Linder et al. |
| 2001/0031989 A1 | 10/2001 | Evans et al. |
| 2002/0016564 A1 | 2/2002 | Courtney et al. |
| 2002/0029077 A1 | 3/2002 | Leopold et al. |
| 2002/0099436 A1 | 7/2002 | Thornton et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0236565 A1 | 12/2003 | DiMatteo et al. |
| 2004/0049226 A1 | 3/2004 | Keegan et al. |
| 2004/0064179 A1 | 4/2004 | Linder et al. |
| 2004/0087965 A1 | 5/2004 | Levine et al. |
| 2005/0154443 A1* | 7/2005 | Linder et al. ............ 623/1.11 |
| 2008/0051541 A1* | 2/2008 | Strickler et al. ............ 526/265 |

FOREIGN PATENT DOCUMENTS

| | | |
|---|---|---|
| DE | 3417738 A1 | 11/1985 |
| DE | 4030998 A1 | 4/1991 |
| EP | 0200688 A1 | 11/1986 |
| EP | 0293605 A1 | 12/1988 |
| EP | 0411118 A1 | 2/1991 |
| EP | 0427429 A2 | 5/1991 |
| EP | 0437121 B1 | 8/1991 |
| EP | 0472334 A1 | 2/1992 |
| EP | 0472368 A2 | 2/1992 |
| EP | 0533511 A1 | 3/1993 |
| EP | 0564894 A1 | 10/1993 |
| EP | 0655228 A1 | 5/1995 |
| EP | 0686379 A2 | 12/1995 |
| EP | 0696447 A2 | 2/1996 |
| EP | 0737450 A1 | 10/1996 |
| EP | 0743046 A1 | 11/1996 |
| EP | 0759287 A1 | 2/1997 |
| EP | 0771549 A2 | 5/1997 |
| EP | 0784988 A1 | 7/1997 |
| EP | 0852132 A1 | 7/1998 |

| | | | |
|---|---|---|---|
| EP | 0737450 | B1 | 11/2003 |
| FR | 2580504 | A1 | 10/1986 |
| FR | 2606642 | A1 | 5/1988 |
| FR | 2643250 | A1 | 8/1990 |
| FR | 2666980 | A1 | 3/1992 |
| FR | 2761592 | A1 | 10/1998 |
| FR | 2768326 | A1 | 3/1999 |
| GB | 2020557 | A | 5/1979 |
| GB | 2020557 | B | 1/1983 |
| JP | 08187294 | A2 | 7/1996 |
| WO | 8809683 | A1 | 12/1988 |
| WO | 9203097 | A1 | 3/1992 |
| WO | 9414389 | A1 | 7/1994 |
| WO | 9419039 | A1 | 9/1994 |
| WO | 9424946 | A1 | 11/1994 |
| WO | 9601591 | A1 | 1/1996 |
| WO | 9604875 | A1 | 2/1996 |
| WO | 9610375 | A1 | 4/1996 |
| WO | 9619941 | A1 | 7/1996 |
| WO | 9623441 | A1 | 8/1996 |
| WO | 9633677 | A1 | 10/1996 |
| WO | 9717100 | A1 | 5/1997 |
| WO | 9727808 | A1 | 8/1997 |
| WO | 9742879 | A1 | 11/1997 |
| WO | 9802084 | A1 | 1/1998 |
| WO | 9802112 | A1 | 1/1998 |
| WO | 9823322 | A1 | 6/1998 |
| WO | 9833443 | A1 | 8/1998 |
| WO | 9834673 | A1 | 8/1998 |
| WO | 9836786 | A1 | 8/1998 |
| WO | 9838920 | A1 | 9/1998 |
| WO | 9838929 | A1 | 9/1998 |
| WO | 9839046 | A1 | 9/1998 |
| WO | 9839053 | A1 | 9/1998 |
| WO | 9846297 | A1 | 10/1998 |
| WO | 9847447 | A1 | 10/1998 |
| WO | 9849952 | A1 | 11/1998 |
| WO | 9850103 | A1 | 11/1998 |
| WO | 9851237 | A1 | 11/1998 |
| WO | 9855175 | A1 | 12/1998 |
| WO | 9909895 | A1 | 2/1999 |
| WO | 9922673 | A1 | 5/1999 |
| WO | 9923976 | A1 | 5/1999 |
| WO | 9925252 | A1 | 5/1999 |
| WO | 9930766 | A1 | 6/1999 |
| WO | 9940964 | A1 | 8/1999 |
| WO | 9942059 | A2 | 8/1999 |
| WO | 9944510 | A1 | 9/1999 |
| WO | 9944542 | A2 | 9/1999 |
| WO | 9955236 | A1 | 11/1999 |
| WO | 9958068 | A1 | 11/1999 |
| WO | 9965417 | A1 | 12/1999 |
| WO | 0007655 | A1 | 2/2000 |
| WO | 0009054 | A1 | 2/2000 |
| WO | 0016705 | A1 | 3/2000 |
| WO | 0020064 | A1 | 4/2000 |
| WO | 0049970 | A1 | 8/2000 |
| WO | 0064356 | A1 | 11/2000 |
| WO | 0067671 | A1 | 11/2000 |
| WO | 0132254 | A1 | 5/2001 |
| WO | 0191844 | A1 | 12/2001 |
| WO | 02083224 | A2 | 10/2002 |
| WO | 03094789 | A1 | 11/2003 |

OTHER PUBLICATIONS

"Endovascular Grafts, Stents Drive Interventional Radiology Growth,"Cardiovascular Device Update, 2(3):1-12 (Mar. 1996).
"Protruding Atheromas in the Thoracic Aortic and Systemic Embolization," pp. 423-427 American College of Physicians (1991).
"Recogntion and Embolic Potential of Intraaortic Atherosclerotic Debris," American College of Cardiology (Jan. 1991).
Cragg, Andrew et al., "A New Percutaneous Vena Cava Filger," AJR, 141:601-604 (Sep. 1983). (4 pages).
Cragg, Andrew et al., "Nonsurgical Placement of Arterial Endoprosthesis: A New Technique Using Nitinol Wire," AJR, pp. 621-263 (Apr. 1983).
Diethrich et al., "Percutaneous Techniques for Endoluminal Carotid Interventions," J. Endovasc. Surg., 3:182-202 (1996). (21 pages).
Fadali, A. Moneim, "A filtering device for the prevention of particulate embolization during the course of cardiac surgery," Surgery, 64(3):634-639 (Sep. 1968).
Haissaguerre et al., "Spontaneous Initiation of Atrial Fibrillation by Ectopic Beats Originating in the Pulmonary Veins," The New England Journal of Medicine, 339(10):659-666 (Sep. 1988).
Jordon, Jr. et al., "Microemboli Detected by Transcranial Doppler Monitoring . . . ," Cardiovascular Surgery, 7(1)33-38 (Jan. 1999).
Lesh, "Can Catheter Ablation Cure Atrial Fibrillation?"ACC Current Journal Review, pp. 38-40 (Sep./Oct. 1997).
Lund et al., "Long-Term Patentcy of Ductus Arteriosus After Balloon Dilation: an Experimental Study,"Laboratory Investigation, 69(4):772-774 (Apr. 1984). (3 pages).
Marache et al., "Percutanous Transluminal Venous Angioplasty . . . ," American Heart Journal, 125(2 P. 1):362-366 (Feb. 1993). (5 pages).
Mazur et al., "Directional Atherectomy with the Omnicath™; A Unique New Catheter System," Catheterization and Cardiovascular Diagnosis, 31:17-84 (1994).
Moussa, MD, Issaam "Stents Don't Require Systemic Anticoagulation . . . But the Technique (and Results) Must be Optimal," Journal of Invasive Cardiol., 8(E):3E-7E, (1996). (5 pages).
Nakanishi et al., "Catheter Intervention to Venous System Using Expandable Metallic Stents,"Rinsho Kyobu Geka, 14 (2);English Abstract Only (Apr. 1994).
Onal et al., "Primary Stenting for Complex Atherosclerotic Plaques in Aortic and Iliac Stenoses,"Cardiovascular & Interventional Radiology, 21(5):386-392 (1998). (7 pages).
Theron et al., "New Triple Coaxial Catheter System for Carotid Angioplasty with Cerebral Protection,"American Journal of Neuroradiology, 11:869-874 (1990). (6 pages).
Tunick et al., "Protruding artherosclerotic plaque in the aortic archo f patients with systemic embolization: A new finding seen by transesophageal echocardiography,"American Heart Journal 120(3):658-660(Sep. 1990). (3 pages).
Waksman et al., "Distal Embolization is Common After Directional Atherectomy . . . ,"American Heart Journal, 129 (3):430-435 (1995). (6 pages).
Wholey, Mark H. et al., PTA and Stents in the Treatment of Extracranial Circulation, The Journal of Invasive Cardiology, 8(E);25E-30E (1996). (6 pages).

* cited by examiner

EMBOLIC FILTER DELIVERY SYSTEM AND METHOD

RELATED APPLICATIONS

This application claims priority to U.S. Provisional Application No. 61/122,575 filed Dec. 15, 2008.

FIELD

This disclosure pertains generally to a delivery system for embolic filters to be deployed in a lumen such as a blood vessel or other duct within the body.

BACKGROUND

Human blood vessels often become occluded or blocked by plaque, thrombi, other deposits, or material that reduce the blood carrying capacity of the vessel. Should the blockage occur at a critical place in the circulatory system, serious and permanent injury, and even death, can occur. To prevent this, some form of medical intervention is usually performed when significant occlusion is detected.

Several procedures are now used to open these stenosed or occluded blood vessels in a patient caused by the deposit of plaque or other material on the walls of the blood vessels. Angioplasty, for example, is a widely known procedure wherein an inflatable balloon is introduced into the occluded region. The balloon is inflated, dilating the occlusion, thereby increasing the intraluminal diameter.

Another procedure is atherectomy. During atherectomy, a catheter is inserted into a narrowed artery to remove the matter occluding or narrowing the artery, i.e., fatty material. The catheter includes a rotating blade or cutter disposed in the tip thereof. Also located at the tip are an aperture and a balloon disposed on the opposite side of the catheter tip from the aperture. As the tip is placed in close proximity to the fatty material, the balloon is inflated to force the aperture into contact with the fatty material. When the blade is rotated, portions of the fatty material are shaved off and retained within the interior lumen of the catheter. This process is repeated until a sufficient amount of fatty material is removed and substantially normal blood flow is resumed.

In another procedure, stenosis within arteries and other blood vessels is treated by permanently or temporarily introducing a stent into the stenosed region to open the lumen of the vessel. The stent typically comprises a substantially cylindrical tube or mesh sleeve made from such materials as stainless steel or nitinol. The design of the material permits the diameter of the stent to be radially expanded, while still providing sufficient rigidity such that the stent maintains its shape once it has been enlarged to a desired size.

Such percutaneous interventional procedures, i.e., angioplasty, atherectomy, and stenting, often dislodge material from the vessel walls. This dislodged material can enter the bloodstream, and may be large enough to occlude smaller downstream vessels, potentially blocking blood flow to tissue.

SUMMARY

The present disclosure pertains to medical embolic protection systems and methods of preparing such medical embolic protection systems for use within a body lumen. The systems of the invention are well suited for delivering medical devices which are self-expanding and which require a low delivery profile such as embolic filters and/or stents. Such devices are often positioned near the distal end of a guide wire, hypotube, or catheter and advanced to, or slightly beyond, an obstruction in the lumen being treated. In some treatment options, the device, or part thereof, may be advanced beyond an obstruction while in other options, the device, or part thereof, may remain proximal of the obstruction. In yet other options, the medical device may be centered with respect to the axial dimension of the obstruction. In each option, it is generally desirable that the medical device be deployed without significant axial movement during deployment which might tend to scrape the lumen wall with an attendant risk of debris generation.

The disclosure also pertains to an embolic filter assembly delivery system having an elongated member and a medical device having a first portion and a second portion disposed axially with respect to the elongated member and near the distal end of the said member. A first portion of the embolic filter assembly device can be mechanically biased toward a radially expanded position and a second portion of the device is less strongly biased toward a radially expanded position. A restraint member, can have one axial gap, a first portion, a second portion, a restraint configuration, and a deployed configuration, is disposed about the medical device wherein the first and second portion of the restraint member are disposed about the first and second portions of the embolic filter assembly, respectively. The first portion of the restraint member can exert a greater restraint force on the embolic filter assembly in the restraint configuration than the restraint force exerted on the embolic filter assembly by the second portion of the restraint member in the restraint configuration. An actuation member interacts with the restraint member in the restraint configuration and is substantially free of interaction with the restraint member in the deployed configuration.

The disclosure also pertains to a method of assembling an embolic filter assembly delivery system having an elongated member with a medical device having a first portion and a second portion disposed axially with respect to the elongated member and near the distal end of the member. The embolic filter assembly has a first portion which is mechanically biased toward a radially expanded position and a second portion which is less strongly biased toward a radially expanded position. A temporary containment sleeve having an interior dimension commensurate with a radially retracted state of the first portion of the embolic filter assembly is placed about the first portion of the medical device while the first portion of the embolic filter assembly is in the radially retracted state. A mandrel having an exterior dimension commensurate with a radially retracted state of the first portion of the embolic filter assembly and a restraint member is disposed about the mandrel such that an axial gap is substantially closed whereupon an activation member bridging the axial gap is provided to engage the restraint member at points on alternating opposite sides of the axial gap. The preformed restraint member is then transferred from the mandrel to the medical device thereby displacing the temporary containment sleeve while replacing it with at least a portion of the restraint member.

DETAILED DESCRIPTION

Figure 1:
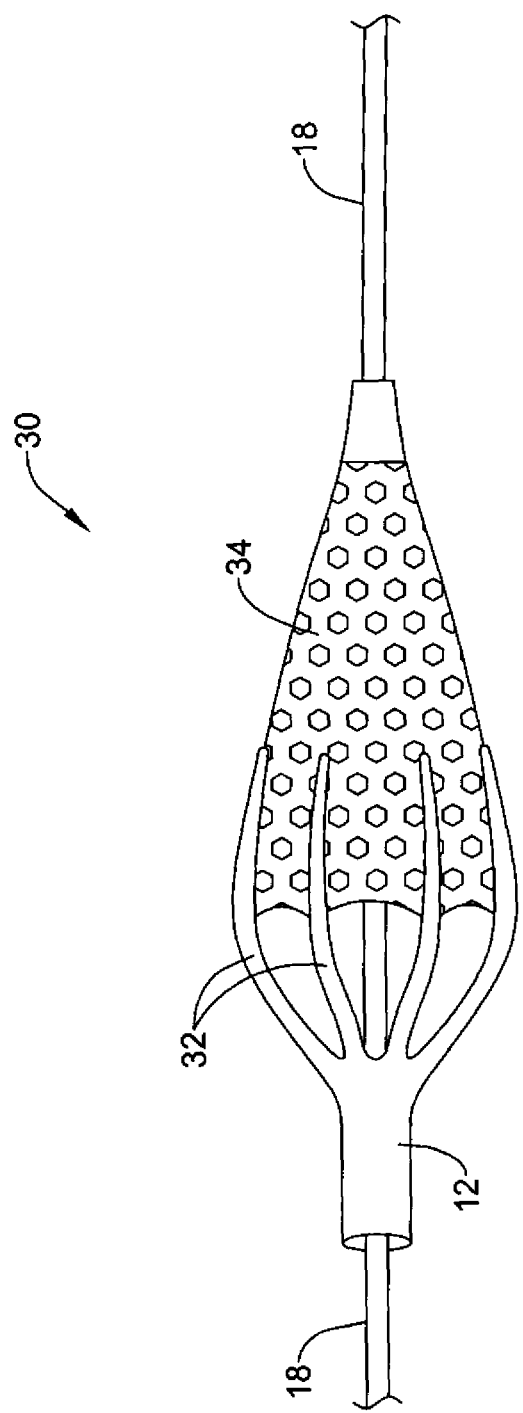
FIG. 1 is an exemplary embolic filter assembly, an embolic filter.

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

One specific example of a medical device which may be delivered by the medical device delivery system disclosed herein, is embolic filter 30, as shown in FIG. 1. The embolic filter 30 includes radially self-expanding struts 32, joined at a hub 12, which support a generally conical filter material 34. The filter material, or basket, is often a membrane or mesh having openings sized to allow blood cells to pass while retaining larger debris such as emboli or dislodged plaque. Materials and methods for assembling embolic filters are known in the art. The embolic filter 30 of FIG. 1 in mounted on guidewire 18. More generally, the embolic filter may be fixed to the guidewire 18 near its distal end or may be advanced along a guidewire, for example by a catheter attached to hub 12. In some embodiments, the embolic filter 30 is attached near the distal end of a catheter or hypotube 28 as shown in the medical device delivery system 10 of FIG. 2. The catheter or hypotube 28 may also serve to contain the proximal and intermediate portions of actuation member 20 which may be activated by withdrawing proximal end 22 of actuation member 20 relative to catheter or hypotube 28.

Figure 2:
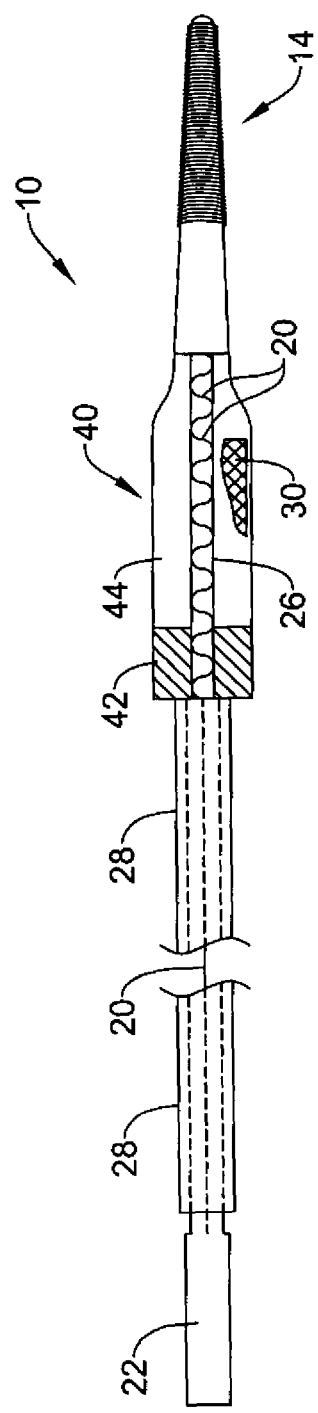
FIG. 2 is an embolic filter assembly in a restraint configuration.

In FIG. 2, embolic filter 30, shown in cutaway, is constrained by restraint member 40 which includes a first portion 42 and a second portion 44 joined along shared axial gap 26 by the laced actuation member 20. Catheter or hypotube 28 extends distally of the constrained filter and terminates in a distal coil 14 or other atraumatic tip. The first portion 42 of restraint member 40 surrounds the radially self-expanding struts 32 (not shown) while the second portion 44 of restraint member 40 surrounds the filter element or basket. First portion 42 of restraint member 40 is formed of materials selected to resist the outward forces exerted by collapsed struts 32. Additional strength in portion 42 may be supplied by material selection, by additional thickness, by reinforcing elements, and the like. Second portion 44 of restraint member 40 is formed of materials which are capable of withstanding the lesser radial forces of the constrained filter element or basket. Accordingly, it may be convenient to fabricate second portion 44 from materials having a lower strength or a lesser thickness.

Figure 3:
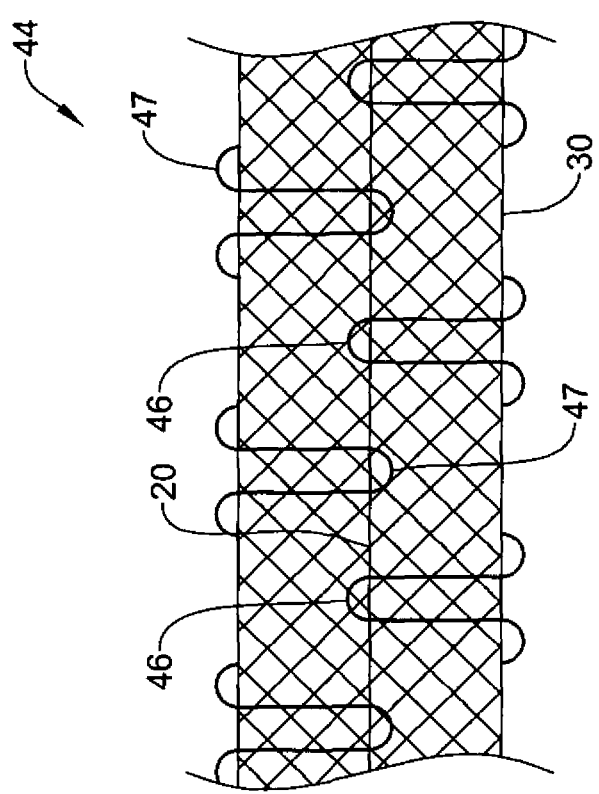
FIG. 3 is a detail of an alternate of a restraint member.

Although the restraint member 40 has been illustrated as a substantially solid sheet, it will be appreciated that other forms of restraint member 40 may be employed. FIG. 3 is a detail of an embodiment of a second portion of restraint member 40 in which the restraint material is formed as a series of loops 46,47 which surround the medical device 30. In this embodiment, the axial gap is formed by "edges" created by the collective loops 46 on one side of the axial gap and collective loops 47 on the other side of the axial gap. Actuation member 20 alternately engages loops 46 and loops 47 to maintain the restraint configuration until actuation member 20 is withdrawn allowing the embolic filter to deploy.

Figure 4:
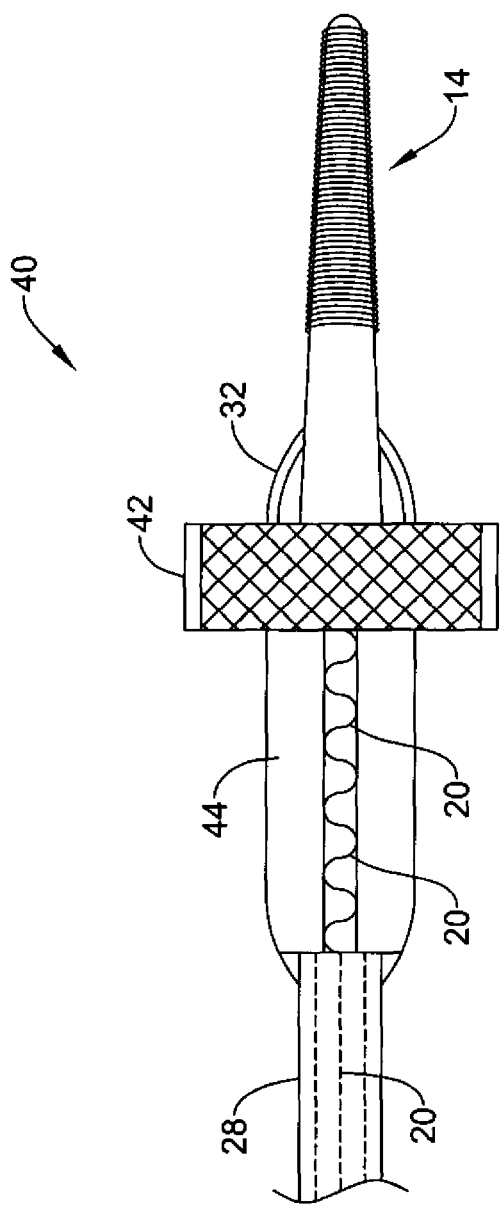
FIG. 4 is an alternate restraint configuration of an embolic filter.

FIG. 4 illustrates an alternate embodiment of a medical device delivery system in which the delivery system has been configured for a staged deployment of the medical device and in which the first portion 42 of restraint member 40 is located distally, rather than proximally, with respect to second portion 44 of restraint member 40. In the case of an embolic filter, this configuration may be used to position the filter within the blood vessel by approaching the protection site within the blood vessel from downstream. In some embodiments, releasing the medical device in a staged sequence may result in a smoother deployment. As illustrated, struts 32 of embolic filter 30 have been partially released from restraint member 40 by withdrawing a second actuation member (not shown) from a second axial gap in first portion 42 of restraint member 40. Alternatively, first portion 42 could have been positioned such that partial withdrawal of actuation member 20 would have released first portion 42 along an axial gap generally corresponding to an extension of axial gap 26. Continued withdrawal of actuation member 20 could then release complete release of second portion 44 of restraint member 40 leading to full deployment of the filter.

As mentioned above, it will be understood that the medical device delivery system may be used to deliver a variety of medical devices and even a plurality of medical devices. In addition to an embolic filter which has already been discussed to an extent, the delivery system may deliver a stent or even a stent and a filter. In such embodiments, one device, for example the stent, may thought of as the portion of the overall medical device which is biased toward a radially expanded position while the filter is the portion of the device which is less strongly biased toward an expanded position. The roles of the stent and the filter may, of course, be reversed in a particular embodiment. Embodiments are envisioned in which the more strongly radially biased portion of the medical device is located distally of the less strongly radially biased portion. Additionally, embodiments are envisioned in which the more strongly radially biased portion of the medical device is located proximally of the less strongly radially biased portion. In yet other embodiments, strongly radially biased portions may alternate with less strongly biased portions. In those embodiments in which multiple medical devices are present, it may be advantageous to provide each medical device with a separate restraint member. It will be appreciated that in those embodiments in which a single restraint member encloses two or more medical devices, the actuation member may partially withdrawn to deploy one medical device component and fully withdrawn to deploy both medical device components.

In some embodiments, the tighter constraint permitted by a restraint member or members of the invention may exacerbate a problem occasionally seen when a constrained medical device includes thermoplastic components. Such components, when subjected to prolonged storage, especially at elevated temperatures occasionally encountered in distribution, may tend to auto-adhere or to cling to other thermoplastic elements within the device. While common fabrication techniques and materials may lead to a preference for the use of thermoplastic elements during assembly of the medical device, it has been found that auto-adhesion within the medical device delivery systems of the invention may be avoided by partially crosslinking the thermoplastic material prior to use. In some embodiments, partial crosslinking may be induced by exposure to ionizing radiation provided by a source producing at least one of electron beam irradiation, gamma irradiation, and ultraviolet irradiation. It has been found that exposure to ionizing radiation may be effective in reducing auto-adhesion when exposure occurs before a medical device containing thermoplastic components is in the restraint configuration and even when exposure to ionizing radiation occurs after the medical device is in the restraint configuration. In some embodiments, it has been found that exposure of the surface of a medical device, or thermoplastic portions thereof, to radiation curable species prior to exposure to ionizing radiation is effective in further reducing auto-adhesion.

The assembly of the medical device delivery system may be facilitated by separately providing the medical device to be delivered in an at least partially collapsed configuration and separately engaging the actuation member with the restraint member to form a structure into which the medical device may be introduced. Returning to the non-limiting example of an embolic filter to be delivered at the distal end of a guidewire, the embolic filter may be affixed to or about the guidewire and optionally exposed to one or more radiation curable species followed by exposure to ionizing radiation. The self-expanding, radially biased struts which support the filter material may then be compressed to lie generally along the guidewire and a temporary containment sleeve or clamp may used to secure the filter in a radially retracted state. It may be desirable at this point to arrange, pleat, or otherwise deploy the filter element in a configuration which efficiently utilizes the space which will be available within the restraint member and which ensures a smooth transition from the compact state to the deployed state as the struts expand.

The restraint member may then be formed around a mandrel having dimensions which approximate the collapsed medical device and the actuation member may be engaged with the restraint member in a state which it is not stressed by the outward bias of the filter struts or any compression of the filter member which may occur when the embolic filter is fully constrained. Once the restraint member assembly is positioned and the actuation member is inserted, the mandrel may be removed. In some embodiments, the mandrel may be used to facilitate transfer of the preformed restraint member assembly to the embolic filter by sliding the restraint member assembly directly from the mandrel onto the constrained embolic filter. The preformed restraint member assembly may be transferred, directly or indirectly, to the embolic filter with simultaneous removal of the temporary containment sleeve. An optional ionizing radiation treatment may also be performed at this point to reduce auto-adhesion during storage and to sterilize the medical device and the device delivery system.

Figure 5A:
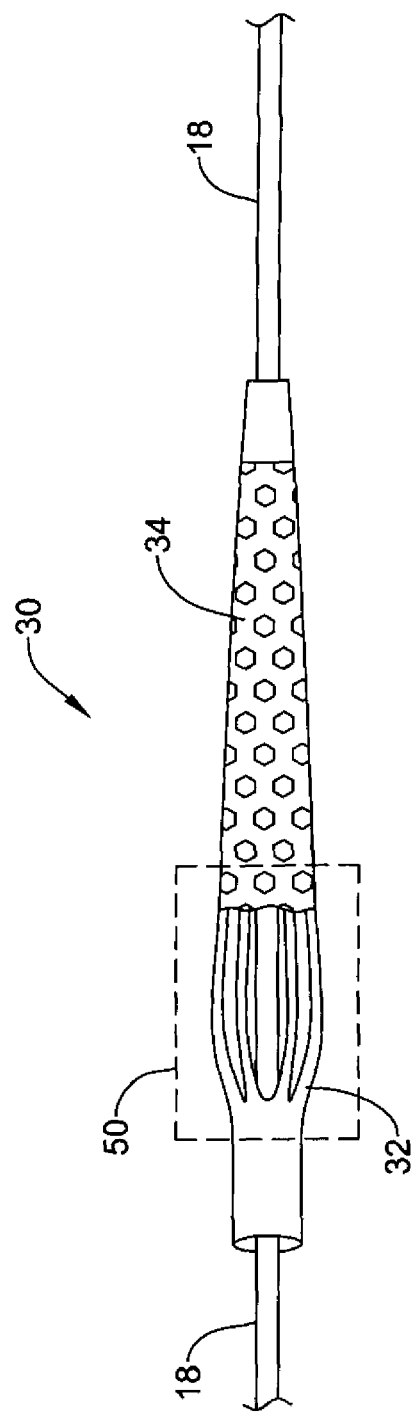
FIG. 5A-D illustrates steps in assembling a embolic filter assembly delivery system.
Figure 5B:
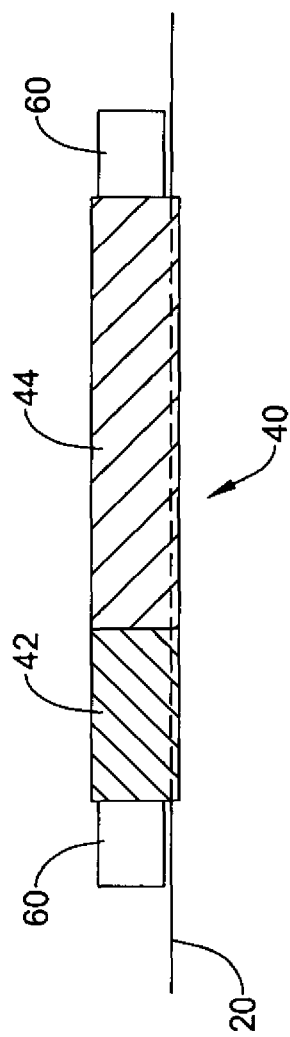
Figure 5C:
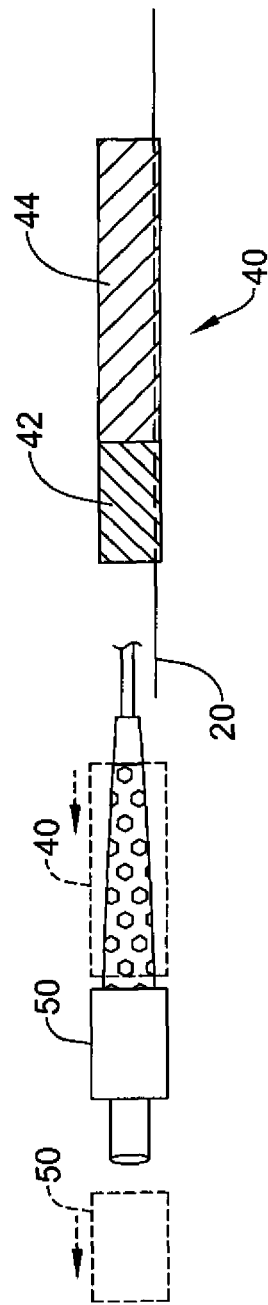
Figure 5D:
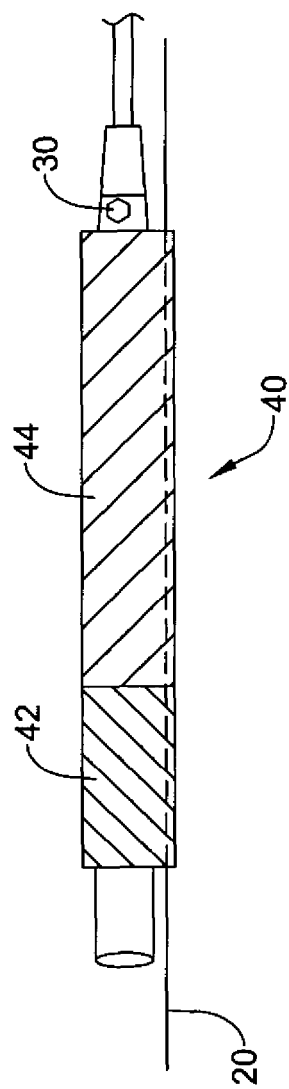

FIGS. 5A-D illustrate a method for the assembly of a medical device delivery system. In FIG. 5A, struts 32 of embolic filter 30 have been collapsed and enclosed in a temporary containment sleeve 50 and filter material 34 has been smoothed into a configuration suitable for being restrained. In FIG. 5B, restraint member 40 has been disposed about mandrel 60 which approximates the desired restraint configuration of embolic filter 30. Actuation member 20 has been engaged with first portion 42 and second portion 44 of restraint member 40 in one of the manners described above or the like. In FIG. 5C, the restraint member, in its restraint configuration is advanced along the embolic filter 30 displacing temporary containment sleeve 50. As illustrated, restraint member 40 was removed from mandrel 60 before it replaces temporary containment sleeve 50 by sliding proximally. It will be appreciated that the transfer may be accomplished by sliding the restraint member 40 directly from the mandrel 60 an over embolic filter 30. In other embodiments of the method, displacement of temporary containment sleeve 50 may be accomplished by sliding the restraint member 40 distally along filter 30, providing that the second portion 44 of restraint member 40 is sufficiently strong to withstand the transitory outward pressure as struts 32 pass through. The constrained embolic filter 30 is illustrated in FIG. 5D.

Figure 6:
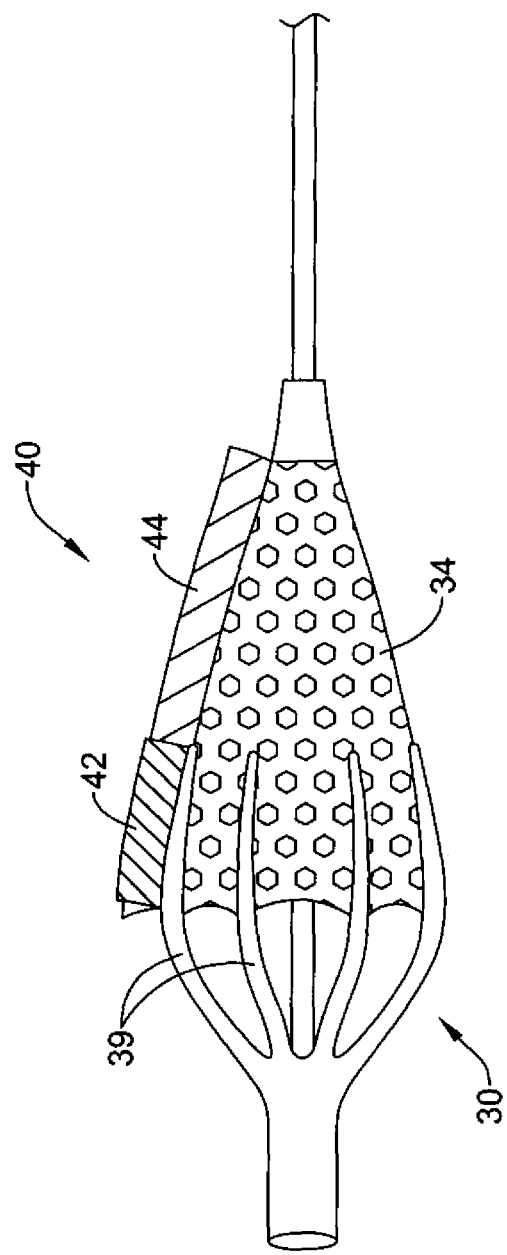
FIG. 6 illustrates a deployed embolic filter assembly.

Following insertion of the medical device delivery system into a lumen and navigation to a desired deployment site, actuation member 20, not shown, may be withdrawn allowing the embolic filter to move from a constrained state to a deployed state as shown in FIG. 6. Although first portion 42 and second portion 44 of restraint member 40 have been shown as fully released and folded back for clarity in illustrating the deployment process, it will be appreciated that when an embolic filter 30 is deployed in a vessel, significant portions of restraint member 40 may lie generally along the filter and/or along the vessel wall where they will not create a significant bypass.

It can be useful to provide a restraint member having two or more portions which differ in the degree of restraint which they provide. In this way, the overall bulk of the restrained medical device delivery system may be reduced while still reliably providing the necessary restraint. In some embodiments, a first portion of the restraint member has a different axial dimension than the second portion reflecting, for example, a relatively short group of collapsed struts may lie adjacent to a relatively longer collapsed filter member. In such configurations, it may be common for the collapsed struts to require a higher total restraining force than the relatively longer collapsed filter member. Accordingly, the material of that portion of the restraining member, and the corresponding actuation member, surrounding the higher force portion of the filter may be formed from higher strength materials and/or from thicker materials. For example, the collapsed struts may advantageously be constrained by a sheet of PEEK (polyetheretherketone) or PET (polyethylene terephthalate), while a thin sheet or even a mesh of polyurethane may suffice to restrain the filter element. Similar considerations may apply to the selection of material for the actuation member which may use, for example wire in the higher force section and thread or polymer in the lower force section. In addition, it may be desirable to arrange for the actuation member to span the gap between the edges of the restraint member more frequently, in an axial sense, in the higher force region and less frequently in the lower force region. This difference in frequency of spanning of the edges of the restraint member by the actuation member may, in some embodiments, suffice to define the two regions of the restraint member. Such changes may be made continuously or in a step-wise fashion. It is believed that the expedient of frequent spannings may lessen the stress at the points of contact between the restraint member and the actuation member and thus reduce the possibility of a premature release.

In some embodiments, the restraint member substantially surrounds at least part of each of the first and second portions of the medical device in the restrained configuration. The restraint member does not necessarily completely enclose the medical device along its entire length or completely envelop its circumference at all points. In certain embodiments, the restraint member substantially surrounds at least part of each of the first and second portions of the medical device in the restraint configuration. In some embodiments, the first portion of the restraint member and the second portion of the restraint member have different circumferential dimensions. Typically, this will reflect the relative dimensions of the portions of the medical device in the restrained configuration; however it may also reflect a design decision related creating a smooth profile to facilitate advancing the restrained device through the lumen, particularly in the vicinity of an obstruction.

In some embodiments, the actuation member, which bridges the axial gap in the restraint configuration, will be completely disengaged from the restraint member in the deployed configuration. In other embodiments, the actuation member may be partially disengaged or merely allowed to loosen to expand the gap. In yet other embodiments, the actuation member may disengage from the restraint member in stages to control deployment of the medical device. It should be understood that the term "axial gap", as used in this document, is to be broadly interpreted to include a variety of configurations of the join between edges of a restraint element. In some embodiments, the gap may not be readily discernable due to overlap of the restraint member edges as in a stitched seam. The term may denote a continuous gap or a sequence of gaps which lie along a line generally parallel to the axis of the elongated member as described below. In the case of cylindrical restraint member, in the restraint configuration, the gap typically would be substantially parallel to the axis of the cylinder and the associated elongated member. In those embodiments where a portion of the restraint member forms a tapered section such as a frustum, an axial gap will be understood to follow generally along a generatrix of the associated cone. In other embodiments, the axial gap may form a helix forming at least a partial turn about a generally cylindrical restraint member. Similarly, the axial gap may assume a generally spiral form around a conical or frustoconical restraint member, or a portion thereof, such that the helix may be thought of as having a decreasing radius in at least one axial direction. In some embodiments, the restraint member may be created by multiple circumferential panels forming multiple axial gaps. Such multiple gaps may share a common actuation member or may employ a multiple actuation members. In some embodiments, portions of the restraint member may alternately cross the axial gap. In such embodiments, the actuation member will typically assume a more nearly linear configuration resembling the pin of a common hinge passing successively through aligned cylinders formed from the restraint member along the edge of the axial gap as in a piano hinge. In other embodiments, the activation member bridges the axial gap by alternately passing through the restraint member at points adjacent to and on opposite sides of the axial gap.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed is:

1. A filter delivery system comprising:
   an elongated member having a distal end and a proximal end;
   a filter having a first portion and a second portion disposed axially with respect to the elongated member and near the distal end of the member wherein a first portion of the filter is mechanically biased toward a radially expanded position and a second portion of the filter is less strongly biased toward a radially expanded position;
   a restraint member having at least one axial gap, a first portion, a second portion, a restraint configuration, and a deployed configuration, wherein the first and second portion of the restraint member are disposed about the first and second portions of the filter, respectively, further wherein the first portion of the restraint member exerts a greater restraint force on the filter in the restraint configuration than the restraint force exerted on the filter by the second portion of the restraint member in the restraint configuration; and
   an actuation member which interacts with the restraint member in the restraint configuration and is substantially free of interaction with the restraint member in the deployed configuration.

2. The filter delivery system of claim 1, wherein the first portion of the restraint member and the second portion of the restraint member have different axial dimensions.

3. The filter delivery system of claim 1, wherein the restraint member substantially surrounds at least part of each of the first and second portions of the filter in the restraint configuration.

4. The filter delivery system of claim 3, wherein the first portion of the restraint member and the second portion of the restraint member have different circumferential dimensions.

5. The filter delivery system of claim 1, wherein the actuation member bridges the axial gap in the restraint configuration and no longer bridges the axial gap in the deployed configuration.

6. The filter delivery system of claim 5, wherein the actuation member bridges the axial gap by alternately passing through the restraint member at points adjacent to and on opposite sides of the at least one axial gap.

7. The filter delivery system of claim 1, wherein the at least one axial gap is substantially parallel to the axis of the elongated member.

8. The filter delivery system of claim 1, wherein the filter comprises a thermoplastic material.

9. The filter delivery system of claim 8, wherein the thermoplastic material is protected from auto-adhesion prior to use by partial crosslinking.

10. The filter delivery system of claim 9, wherein the partial crosslinking is induced by exposure to ionizing radiation.

11. The filter delivery system of claim 10, wherein the ionizing radiation is provided by a source producing at least one of electron beam irradiation, gamma irradiation, and ultraviolet irradiation.

12. The filter delivery system of claim 10, wherein the exposure to ionizing radiation occurs before the filter is in the restraint configuration.

13. The filter delivery system of claim 10, wherein the exposure to ionizing radiation occurs after the filter is in the restraint configuration.

14. The filter delivery system of claim 10, wherein the exposure to ionizing radiation occurs after the surface of the thermoplastic has been exposed to a radiation curable species.

* * * * *